US00PP11358P

United States Patent [19]

Lawley

[11] Patent Number: Plant 11,358

[45] Date of Patent: Apr. 25, 2000

[54] CAMPANULA PLANT NAMED 'FRANK LAWLEY'

[75] Inventor: Frank Lawley, Cambo, United Kingdom

[73] Assignee: Blooms of Bressingham Ltd., Norfolk, United Kingdom

[21] Appl. No.: 09/035,901

[22] Filed: Mar. 6, 1998

[51] Int. Cl.[7] ..... A01H 5/00

[52] U.S. Cl. ..... Plt./263

[58] Field of Search ..... Plt./263

[56] References Cited

U.S. PATENT DOCUMENTS

P.P. 9,815 3/1997 Bourke et al. ..... Plt./263

*Primary Examiner*—Howard J. Locker

*Assistant Examiner*—Wendy A Baker

*Attorney, Agent, or Firm*—Foley & Lardner

[57] ABSTRACT

A new and distinct cultivar of Campanula plant named 'Frank Lawley', characterized by its large deep violet blue cup and saucer type flowers which bloom beginning in June and continuing well into August, dark green foliage, and its adaptability to cut flower production as well as being an excellent cultivar for border or container use.

1 Drawing Sheet

The present invention relates to a new and distinct cultivar of hardy perennial herbaceous plant of the genus Campanula, known by the cultivar name 'Frank Lawley'. The genus is a member of the Campanulaceae family.

The new cultivar originated as a seedling discovered by the inventor Frank Lawley in Morpeth, Northumberland, England and resulted from a cross made by the inventor between *C. persicifolia* 'Cup and Saucer White'(unpatented), an Award of Garden Merit cultivar as the female parent, and a proprietary cultivar of *C. persicifolia* as the male parent.

The first act of asexual reproduction of 'Frank Lawley' was accomplished when basal cuttings were taken by the inventor in Morpeth, England. This and subsequent asexual reproduction by division and basal cuttings have shown that the unique combination of characteristics as herein disclosed for 'Frank Lawley' are fixed and retained through successive generations of asexual reproduction.

'Frank Lawley' has not been observed under all possible environmental conditions. The phenotype may vary with variations in environment such as temperature and light intensity without, however, any variance in the genotype.

The following observations and measurements describe the plants grown in Morpeth, Northumberland, England under normal commercial practice.

The following traits have been repeatedly observed and are determined to be basic characteristics of the new cultivar, which in combination distinguish the new cultivar from others:

1. It is a quality flowering perennial combining the cup and saucer flowering habit of the female parent with the deep violet blue classic bell flowers of the typical *C. persicifolia* form. The new cultivar therefore makes excellent cut flowers.

2. The new cultivar produces evergreen clumps which flower for many weeks starting in mid-June and continuing through late August.

3. The narrow evergreen basal rosettes of leaves make a pleasing backdrop to the erect wiry stems carrying the flowers.

4. The flower comprises a large bell-shaped cup with a flattened bell-shaped saucer underneath the cup, hence the "cup and saucer" flowering habit.

5. The plant thrives best in full sun but will tolerate part shade in well drained soil that does not become too dry.

The accompanying color photograph comprises a close-up view of the new cultivar emphasizing the flower shape and color. The photograph does not accurately depict the color value of the flower which is deep violet-blue, R.H.S. 94A.

In the following is a detailed description of the new cultivar based on plants grown in Morpeth, England. All color determinations are based on The Royal Horticultural Society Colour Chart.

Plant origin: Seedling selection.

Parentage: A cross between *C. persicifolia* 'Cup and Saucer White' and a proprietary cultivar of *C. persicifolia*.

Habit: Clump forming.

Size: Mature plants are approximately 90 cm in height with a spread of 40 cm.

Root system: Fibrous.

Plant vigor: The new perennial shows vigorous and healthy growth throughout Great Britain. Each plant will form a clump by the end of the growing season. A single cutting would make up to 50% of its mature spread in the first growing season.

Blooming habit: Large showy deep violet blue flowers, borne on erect racemose stems arising from the base of the plant.

Blooming period: From June continuing into August.

Hardiness: Winter hardy throughout Great Britain. The plant has not been fully tested for maximum summer temperature tolerance above 32° C. (90° F.).

Flowers:

*Petal count.*—Five individual cup shaped petals of equal size, and five equal size flattened saucer type petals.

*Flower shape.*—Campanulate, consisting of a bell shaped cup and a saucer formed from a bell shaped flower that has flattened out to form a saucer shaped disc complete with petals.

*Flower type.*—Racemose.

*Flower size.*—6 cm in diameter.

*Carpels.*—3–5 celled.

*Stamens*.—5 per flower, yellow in color, 1B.

*Pedicel*.—Approximately 4 to 8 cm long.

*Flower buds*.—Elliptic, heavily ribbed, approximately 2 cm long and 1 cm wide.

*Lastingness of individual bloom*.—Each flower lasts for up to 10 days.

*Raceme*.—Approximately 25 flowers per raceme and 5 to 8 racemes per plant. All racemes would have formed by the second week of flowering.

*Color*.—The petals of mature flowers are 94A in color.

Foliage:

*Shape*.—Linear lanceolate to subulate, and finely and remotely crenulated.

*Type*.—Evergreen perennial.

*Texture*.—Smooth and without hairs.

*Length*.—10–15 cm.

*Width*.—2 cm.

*Petiole length*.—2 cm.

*Margins*.—Crenate.

*Apex*.—Acuminate.

*Base*.—Truncate.

*Color*.—Mature leaves, upper surface 131A, lower surface 137C.

I claim:

1. A new and distinct cultivar of Campanula plant named 'Frank Lawley', as illustrated and described.

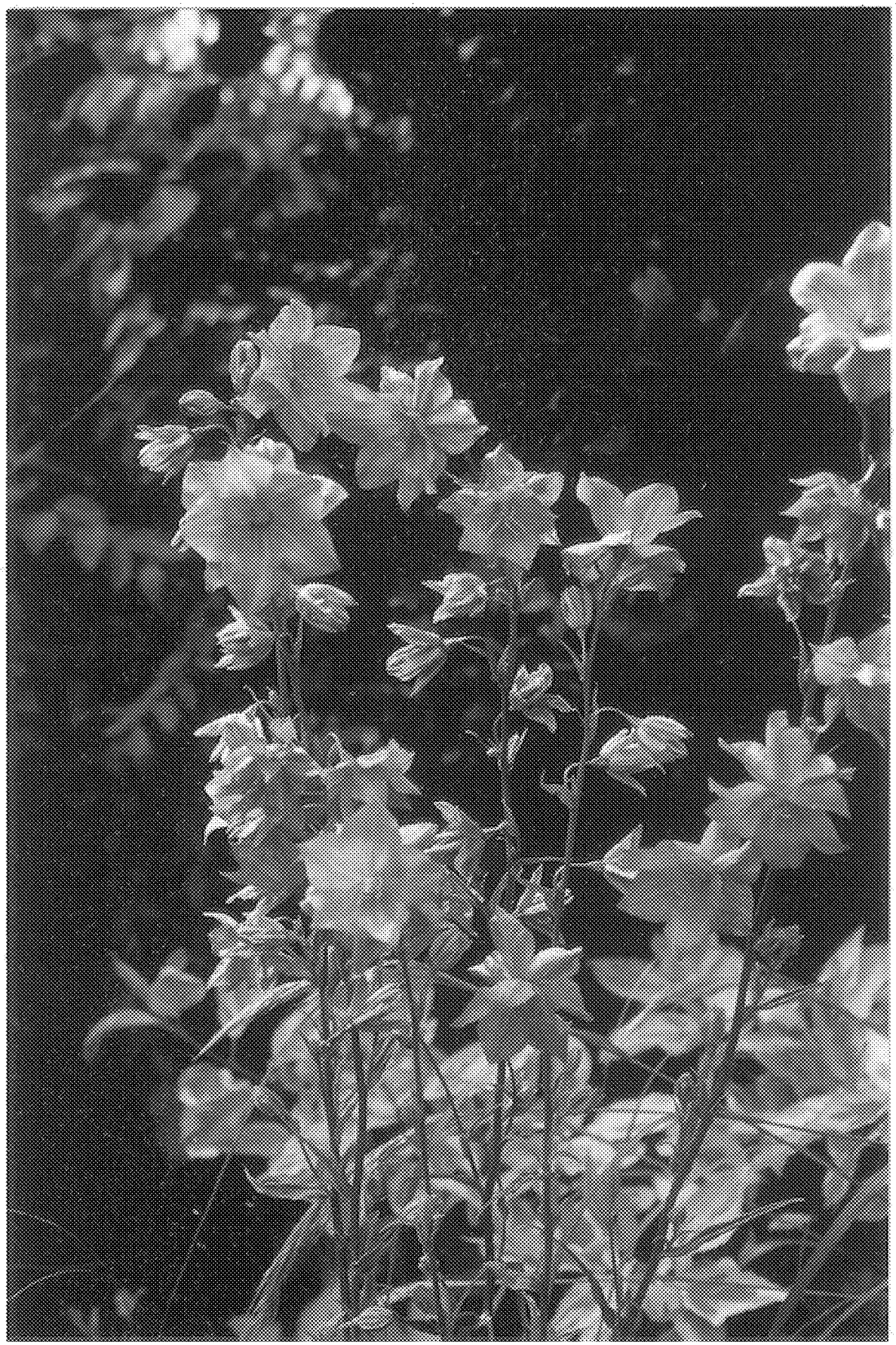

* * * * *